United States Patent [19]

Heimer et al.

[11] Patent Number: 4,957,737
[45] Date of Patent: Sep. 18, 1990

[54] HTLV-III (LAV) ENVELOPE PEPTIDES

[75] Inventors: Edgar P. Heimer, Sparta; Premkumar E. Reddy, Montclair, both of N.J.

[73] Assignee: Hoffmann-La Roche Inc., Nutley, N.J.

[21] Appl. No.: 396,195

[22] Filed: Aug. 21, 1989

Related U.S. Application Data

[63] Continuation of Ser. No. 160,847, Feb. 1, 1988, abandoned, which is a continuation of Ser. No. 866,817, May 27, 1986, abandoned.

[51] Int. Cl.$^5$ ..................... A61K 39/12; A61K 37/02; C07K 7/10
[52] U.S. Cl. ...................... 424/88; 530/324; 530/403; 530/806; 530/807; 514/12
[58] Field of Search ............... 530/324, 403, 806, 807; 514/12; 424/88

[56] References Cited

U.S. PATENT DOCUMENTS

| | | | |
|---|---|---|---|
| 4,629,783 | 12/1986 | Cosand | 530/324 |
| 4,772,547 | 9/1988 | Heimer et al. | 435/5 |
| 4,774,175 | 9/1988 | Chang et al. | 530/324 |

OTHER PUBLICATIONS

Chang et al., Bio/Technology, vol. 3, pp. 905–909 (1985).
Wang et al., Proc. Natl. Acad. Sci., U.S.A., vol. 83, pp. 6159–6163 (1986).
Sarngadharan et al., Science, vol. 224, pp. 506–508 (1984).
Ratner et al., Nature, vol. 313, pp. 277–284 (1985).
Sanchez-Pescador et al., Science, vol. 227, pp. 484–492 (1985).
Wain-Hobson et al., Cell, vol. 40, pp. 9–17 (1985).
Kiyokawa et al., Proc. Natl. Acad. Sci., U.S.A., vol. 81, pp. 6202–6206 (1984).
Zagury et al., III International Conference on Aids, T-16-5 (1987).
Fauci, PNAC, U.S.A., vol. 83, pp. 9278–9283 (12/86).
Crowl et al., Cell, vol. 41, p. 979 (7/85).
Shaw et al., Science, vol. 226, p. 1165 (1984).
Veronese et al., Science, vol. 229, p. 1402 (1985).
Muesing et al., Nature, vol. 313, p. 450 (1985).
Hahn et al., Nature, vol. 312, No. 8, p. 166 (1984).
Schupbach et al., Science, vol. 224, p. 503 (1984).
Rosen et al., Dictionary of Immunology, Stockton Press, p. 110 (1989).

*Primary Examiner*—Lester L. Lee
*Assistant Examiner*—Christina Chan
*Attorney, Agent, or Firm*—George M. Gould; William H. Epstein; Patricia S. Rocha

[57] ABSTRACT

Synthetic peptides containing the epitopic sequence HTLV env (578–608) are useful as reagents in immunoassays for detection of AIDS antibodies, as immunogens for eliciting polyclonal or monoclonal antibodies against AIDS virus env protein and as components in an AIDS vaccine.

4 Claims, No Drawings

HTLV-III (LAV) ENVELOPE PEPTIDES

This application is a continuation of U.S. patent application Ser. No. 160,847, filed Feb. 1, 1988, now abandoned, which is a continuation of U.S. patent application Ser. No. 866,817, filed May 27, 1986, now abandoned.

FIELD OF THE INVENTION

This invention relates to synthetic peptides, designated HTLV-III env whose sequence represent a conserved region of the viral envelope protein of the etiologic agent for Acquired Immune Deficiency Syndrome (AIDS), derivatives of such peptides and the use of such peptides and/or derivatives in methods for detecting the presence of AIDS antibodies in human blood. The region of the envelope protein from which such peptides have been selected is believed to contain sequences that are responsible for immunosuppression properties of the virus. Such peptides can be utilized in immunogenic compositions which can be used as vaccines or to elicit antibodies in host animals, which antibodies in turn can be employed to detect the HTLV-III virus in biological fluid specimens.

The results disclosed herein are based in part on the techniques and concepts of the field of immunology. For convenience, certain terms commonly used in the art are defined herein. The term "immunochemical reaction" is used to denote the specific interaction which occurs between an antigen and its corresponding antibody, regardless of the method of measurement. Such a reaction is characterized by a non-covalent binding of one or more antibody molecules to one or more antigen molecules. The immunochemical reaction may be detected by a large variety of immunoassays known in the art. The terms "immunogenic" or "antigenic" will be used here to describe the capacity of a given substance to stimulate the production of antibodies specifically immunoreactive to that substance when that substance is administered to a suitable test animal under conditions known to elicit antibody production. The term "protective antigen" refers to the ability of a given immunogen to confer resistance in a suitable host, against a given pathogen. The term "epitope", refers to a specific antibody binding site on an antigen. Macromolecular antigens such as proteins typically have several epitopes with distinctive antibody binding specificities. Different epitopes of the same antigen are distinguishable with the aid of monoclonal antibodies which, due to their high degree of specificity, are directed against singly epitopes. Two different monoclonal antibodies directed against different epitopes on the same antigen may each bind the antigen without interfering with the other, unless the epitopes are so close together that the binding of one sterically inhibits the binding of the other. The term "immunodominant region" denotes an area of the antigen molecule which is mainly responsible for its antigenicity.

BACKGROUND OF THE INVENTION

From 1981 to date, there have been over eighteen thousand (18,000) people diagnosed as having acquired immune deficiency syndrome (AIDS). AIDS has been characterized by the onset of severe opportunistic infections secondary to an effect on the body's immune system. Gottlieb, M. S. et al., Pneumocystis Carinic Pneumonia and Mucosal Candidisis in previously healthy homosexual men: evidence of a new acquired cellular immuno-deficiency, N. Eng. J. Med. 305, 1426-1431 (1981). The disease has been found in male homosexuals, patients receiving blood products, intravenous drug addicts, and individuals originating from Haiti and Central Africa. Piot, P. et al, Acquired immuno-deficiency syndrome in a heterosexual population in Zaire. Lancet 11, 65-69 (1984). The causative agent was suspected to be of viral origin as the epidemiological pattern of AIDS was consistent with a transmissable disease. At least three (3) retroviruses have been isolated from cultured T-cells of several patients with AIDS, or from white blood cells of persons at risk for the disease. A novel human retrovirus called lymphadenopathy-associated virus (LAV) was discovered and its properties were consistent with its etiological role in AIDS. That virus was isolated from a patient with lymphadenopathy and hence the name. Montagnier, L. et al. A New Human t-lymphotropic retrovirus: Characterization and possible role in lymphadenopathy and acquired immune deficiency syndromes. In Human T-Cell Leukemia/Lymphoma Virus, R. C. Gallo, M. Essex and L. Gross, eds. (Cold spring Harbor, N.Y.: Cold Spring Harbor Laboratory) pp. 363-370. Other human retroviruses, specifically two subgroups of the human t-cell leukemia/lymphoma/lymphotropic virus, types I and III have been isolated. (HTLV I: Poicsz, B. J. et al. PNAS (USA) 77, 7415 (1980)); (HTLV-III: Popovic, M. et al. Detection, isolation and continuous production of cytopathic retroviruses (HTLV-III) from patients with AIDS and pre-AIDS. Science 224, 797-500 (1984)). Still another virus, the AIDS associated retrovirus (ARV), was proposed as the causative agent. Levy, J. A. et al. Isolation of lymphocytopathic retroviruses from San Francisco patients with AIDS. Science 225, 840-842 (1984)). Both the HTLV-III and ARV retroviruses display biological and sero-eidemiological properties similar to LAV. Levy et al., supra, Popovic et al. supra. As seen from the above, at least three (3) retroviruses have been postulated as the etiologic agent or AIDS: LAV; ARV; and, HTLV subtypes I and III.

LAV, HTLV III and ARV-II genomes have been molecularly cloned. Shaw, G. M. et al., Serological analysis of a subgroup of human T-lymphotropic retroviruses (HTLV III) associated with AIDS. Science 224, 503-505 (1984). Alizon, M. et al. Molecular Cloning of lymphadenopathy - associated virus. Nature, in press. The complete nucleotide sequence of the proviral genome of LAV, ARV and HTLV III has been determined. Ratner, L. et al. Complete nucleotide sequence of the AIDS virus, HTLV III. Nature 313, 277-284 (1985); Sanchez-Pescadov, R. et al. Nucleotide sequence and expression of an AIDS-associated retrovirus (ARV-2). Science 227, 484-492 (1985); and, Wain-Hobson, S. et al. Nucleotide sequence of the AIDS virus, LAV. Cell 40, 9-17 (1985).

One reason for the difficulty in determining the etiologic agent of AIDS was due to the reactivity of various retroviral antigens with serum samples from AIDS patients. For example, serum samples from AIDS patients have been shown to react with antigens of HTLV I and HTLV III. (HTLV-I: Essex, M., et al., "Antibodies to Cell Membrane Antigens Associated with Human T-Cell Leukemia Virus in Patients with AIDS", Science 220, 859(1983)); (HTLV-III: Sarngadharan, M. G. et al., "Antibodies Reactive With Human T-Lymphotropic Retroviruses (HTLV-III) in the Serum of Patients With AIDS", Science 220, 506–508 (1984)). Envelope gene products of HTLV demonstrated antigenicities cross-reactive with antibodies in sera from adult T-cell leukemia patients. Kiyokana, T. et al. "Envelope proteins of human T-cell leukemia virus: Expression in *Escherichia coli* and its application to studies of env gene functions" PNAS (USA) 81, 6202–6206 (1984). Adult T-cell leukemias (ATL) differ from acquired immune deficiency syndrome (AIDS) in that HTLV-I causes T-cell malignancies, that is uncontrolled growth of T-cell. In AIDS rather than cell growth there is cell death. In fact this cytopathic characteristic of HTLV III was critical to determining ultimately the specific retroviral origin of the disease. Thus the etiologic agent of AIDS was isolated by use of immortalized human neoplastic T cell lines (HT) infected with the cytopathic retrovirus characteristic of AIDS, isolated from AIDS afflicted patients. Sero-epidemiological assays using this virus showed a complete correlation between AIDS and the presence of antibodies to HTLV III antigens. Gallo et al. supra 1984; Sarngadharan et al. supra 1984; Schupbach et al. Serological Analysis of a subgroup of human T-lymphotropic retroviruses (HTLV III) associated with AIDS, Science 224, 503–505 (1984). In addition, nearly 85% of patients with lymphadenopathy syndrome and a significant proportion of asymptomatic homosexual men in AIDS endemic areas were also found to carry circulating antibodies to HTLV III. Taken together, all these data indicate HTLV III to be the etiologic agent for AIDS.

Until the successful culturing of AIDS virus using H-9 cell line the env AIDS protein of the AIDS virus had not been isolated, characterized or synthesized. This, in a major part, is due to the fact that the virus is cytopathic and thus isolation of the virus was not possible. Popovic, M. et al., Detection, Isolation, and Continuous Production of Cytopathic Retroviruses (HTLV III) From Patients With AIDS and Pre AIDS, Science 224, 497–500 (1984). Once the human T-cell line resistant to the cytopathic effects of the virus was discovered, a molecular clone of proviral DNA could be achieved.

The need for a sensitive and rapid method for the diagnosis of AIDS in human blood and its prevention by vaccination is very great. Virtually all the assays/tests presently available are fraught with errors. In fact the Center for Disease Control (CDC) has indicated that presently available tests be used solely for screening units of blood for antibody to HTLV III. The CDC went further by stating that the presently available ELISA tests not be used for general screening of high risk populations or as a diagnostic test for AIDS. Federal Register 50(48), 9909, Mar. 12, 1985. The errors have been traced to the failure to use a specific antigenic protein of the etiologic agent for AIDS. The previously used proteins were derived from a viral lysate. Since the lysate is made from human cells infected with the virus, i.e. the cells used to grow the virus, the lysate will contain human proteins as well as viral proteins. Thus preparation of a pure antigen of viral protein is very difficult. The antigen used produced both false positive and false negative results. Budiansky, S., AIDS Screening, False Test Results Raise Doubts, Nature 313, 583(1984).

The errors caused by the use of such lysate proteins/peptides can be avoided by using a composition for binding AIDS antibodies which is substantially free of the non-AIDS specific proteins. Compositions that are substantially pure HTLV-III env peptide fragments of the present invention can be used as antigens. The HTLV-III env peptides of the instant invention encompass a highly conserved epitope sequence designated HTLV-III env (578-608) which permit their use to screen for and diagnose and/or prevent by vaccination the AIDS virus.

A synthetic peptide representing HTLV-III env (477-491) and its use as an immunogen for production of monoclonal antibodies which specifically bind to the envelope region of HTLV-III and which are used in a diagnostic reagent in an enzyme linked immunosorbent assay are described in U.S. patent application Ser. No. 779,431, filed Sept. 24, 1985, title HTLV-III/LAV Synthetic Peptide, Inventors F. Wong-Staal et al., pending.

Synthetic peptides containing the sequence HTLV-III env (500-511) and their use as an immunogen for the production of vaccines and diagnostic reagents for detection of antibodies to the virus etiological agent for AIDS are described in U.S. patent application Ser.No. 824,913 filed Feb. 3, 1986 titled HTLV-III Envelope Peptides, inventors Gallo et al., now U.S. Pat. No. 4,772,547.

DESCRIPTION OF THE INVENTION

The peptides of the present invention can be represented by the following formula:

W-X-Ala-Arg-Ile-Leu-Ala-Val-Glu-Arg-Tyr-Leu-
Lys-Asp-Gln-Gln-Leu-Leu-Gly-Ile-Trp-Gly-Cys-
Ser-Gly-Lys-Leu-Ile-Cys-Thr-Thr-Ala-Val-Y-Z where W is H-, Cys- or Tyr-, X is a bond or a sub-sequence of one or more amino acids starting from the carboxyl terminus of HLTV-III env (557-577), Y is a bond or a sub-sequence of one or more amino acids starting from the amino terminus of HTLV-III env (609-641), and Z is —OH, —NH$_2$ —Cys—NH$_2$, provided however that one of X or Y is a bond.

The derivatives of the peptide of formula I having cysteine at either the amino or the carboxy terminus are utilized to provide improved coupling of the peptide to immunogenic carrier materials when the peptide is to be utilized as an immunogen to elicit antibody formation. The derivatives of formula I, wherein W is tyrosine, provide a preferred substrate for radio-iodination thereby allowing such compounds to be utilized as radio-labelled ligands in a radioimmunoassay for HTLV-III antibody in test fluids.

A preferred aspect of the compounds of the present invention is obtained by compounds of formula I wherein X is a bond and Y is a bond. Thus, a particularly preferred species of this invention is HTLV-III env (578-608) that is a compound of formula I where W and Z are H- and -OH respectively and X and Y are each a bond.

Compounds of the present invention of formula I can be conveniently prepared by utilizing conventional solid phase peptide synthesis methods well-known in the art. In such synthetic method, a polymeric solid-phase support to which the amino acids used in the synthesis are covalently anchored in sequence starting from the carboxyl terminus is used. Automated solid-phase peptide synthesizers suitable for carrying out such methodology are commercially available and synthesis is carried out according to the instructions of the manufacturer. In the event an amide group is desired at the carboxyl terminus for compounds of formula I, then the resin employed is a benzylhydrylamine resin which is an article of commerce. Cleavage of the peptide chain from such resin results in the formation of an amide group as desired at the carboxyl terminus.

Upon completion of the automated peptide synthesis, the desired peptides are removed from the resin utilizing methods well-known in the art, e.g. anhydrous liquid HF. This treatment also cleaves off any side chain protecting groups. The product peptide can then be purified in conventional manner, such as, for example, by utilizing high performance liquid chromatography preferably with a reverse phase $C_{18}$ type column.

DETAILED DESCRIPTION OF THE INVENTION

In accordance with the present invention, the search for the env protein of the etiologic agent for Acquired Immune Deficiency Syndrome (AIDS) has lead to the isolation and sequencing and expressing of the proviral gene of the AIDS virus. It has now been discovered, that the postulated etiologic agents of AIDS, lymphadenophathy-associated virus (LAV), AIDS-associated - retrovirus (ARV) and human T-cell leukemia/lympha/lymphotropic virus, HTLV-III, are in fact variants of the same virus. For purposes of this invention and claims, the virus causing AIDS will be referred to herein as AIDS virus. AIDS virus will be understood to include the variants which have been postulated as the causative agent of AIDS, namely, LAV, ARV and HTLV-III. The env protein of the AIDS virus (env AIDS) is a 97,200 dalton protein with 32 potential N-glycosylation sites. Nucleotide sequence analysis of the AIDS env. gene of the putative etiologic agents of AIDS demonstrates that all the viruses are variants of the same virus. There has been found to be approximately 1 to 20% divergents of variation from the sequence from the env. gene of HTLV-III and the sequences of the env. genes of the other viruses LAV and ARV-II.

The intergrated proviral genome of HTLV-III was cloned from the genomic DNA of H9 cells infected with HTLV-III. See Shaw et al., Science 226, 1165–1171 (1984). The comparative nucleotide sequences of LAV, ARV-II and HTLV-III have been determined by Ratner, Nature 313, 277–284 (1985); Sanchez-Pescadov et al., Science 227, 484–492 (1985); and Wain-Hobson et al., Cell 40, 9–17 (1985) respectively.

One of the conserved regions in these various viral env. gene sequences is the region corresponding to amino acids 558–628 which contains the important epitopic site around 578–608. It is thus believed that such region provides a preferred antigenic site for use in detection of the presence of AIDs viruses or antibodies directed thereto present in the sera of human subjects.

In one diagnostic embodiment of the present invention, the peptides of formula I can be employed in a sandwich type enzyme immunoassay to directly detect the presence of antibody to AIDS virus in serum samples. Such assay can be carried out quite simply by coating microtiter plates with a dilute solution of a peptide of formula I, preferably where W is H and Z is —$NH_2$ or Cys—$NH_2$. The peptide coated microtiter plates can then be incubated with the test sample for sufficient time to allow any antibody present to complex with the peptide. After the incubation period has been completed, the serum sample is removed, the plates are washed and then treated with anti-human IgG coupled to an enzyme such as horseradish peroxidase. Such reagents are articles of commerce. If any antibody to AIDS virus is present in the serum sample, it will be bound by the peptide and will be complexed to the anti-human IgG bearing the enzyme label. After removal of the reagent, substrate for the enzyme is added and allowed to incubate in the microtiter plate. If antibody were present in the sample, a color reaction will be observed in the microtiter plate.

In an alternative diagnostic embodiment, compounds of formula I wherein W is tyrosine are radioiodinated in a conventional manner such as, for example, by use of chloramine-T utilizing $^{125}I$ as the radioactive ligand. Antibodies specific for AIDS virus can be obtained by utilizing compounds of formula I where either W or Z is cysteine as haptens in the preparation of an immunogenic composition. Such immunogenic composition is prepared by bonding the aforesaid haptens through the indicated cysteine moiety to a conventional immunogenic carrier material. As used herein, the term "immunogenic carrier material" is meant to include those materials which have the property of independently eliciting an immunogenic response in a host animal and which can be covalently coupled to the above described haptens preferably through said cysteine moiety. Suitable carrier materials include, for example, proteins; natural or synthetic polymeric compounds, such as, polypeptides, e.g., polylysine or copolymers of amino acids, polysaccharides; and the like. Particularly preferred carrier materials are proteins and polypeptides, especially proteins.

The identity of the protein material utilized in the preparation of an immunogen useful in the instant invention is not critical. Examples of suitable proteins useful in the practice of this invention include mammalian serum proteins such as, for example, thyroglobulin human gamma globulin, human serum albumin, bovine serum albumin, methylated bovine serum albumin, rabbit serum albumin and bovine gamma globulin and keyhole limpet hemocyanin. A particularly preferred protein for this purpose is thyroglobulin.

The covalent coupling of the peptide hapten to the immunogenic carrier material can be carried out in a manner well-known in the art. Reagents suitable for this purpose include N-succinimide esters, carbodiimides, EEDQ(N-ethoxycarbonyl-2-ethoxy-1,2-dihydroquinoline) and the like. A particularly preferred reagent for use in coupling the peptide hapten to the keyhole limpet hemocyanin of the preferred embodiment is m-maleimido- benzoyl-N-succinimide ester.

The aforesaid immunogen may be utilized to induce formation of antibodies specific to AIDS virus in host animals by injecting the immunogen in such a host preferably using an adjuvant known in the art such as complete or incomplete Freund's adjuvant. Improved titers can be obtained by repeated injections over a period of time. Suitable host animals for this purpose include mammals such as, rabbits, horses, goats, guinea pigs, rats, cows, sheep, etc. The resulting antiserum will contain antibodies which will selectively complex with AIDS virus, e.g. HTLV-III preparations containing the env (578–608) epitope. The anti-serum can be affinity purified in a manner known per se by passing such anti-serum over an affinity column prepared from a peptide of formula I, preferably where W is Cys, coupled to a solid support matrix such as Sepharose.

In a further aspect of this invention it is possible to produce monoclonal antibodies specific to the aforesaid 578–608 epitope of the env gene of HTLV-III. The production of monoclonal antibodies can be carried out according to the general procedure described by Kohler and Milstein, Nature 256, 495–597 (1975). The resulting hybrid cells produced by this method have the property of secreting an antibody of predefined specificity. This specificity is that of the antibody produced by lymphocytes involved in the fusion. The hybrid cells may be cloned and grown in stable culture to produce in the culture supernatant samples of antibody to a specific determinant or epitope.

The general method of production of hybrid cell lines of the type described above comprises the steps of immunizing an animal (usually a rat or mouse but not necessarily one of those) with the described immunogen, i.e. a peptide of formula I wherein W or Z is cysteine covalently bonded to an immunogenic carrier material. After allowing time for the immune system to generate lymphocytes secreting the antibody to the immunogen, the animal is sacrificed and a suspension of the spleen is prepared. Fusion between these cells and myeloma cells is achieved by bringing them into contact in the presence of a fusion promoter (e.g. polyethylene glycol). A small percentage of the cells fuse to produce hybrid myeloma cells. The immunization results in a plurality of different lymphocytes each secreting antibody to a different antigenic determinant, and these characteristics are transferred genetically to the hybrid cells. It is possible, by careful screening, to isolate from a culture of hybrid cells, a cell having the desired specificity to the 578–608 epitope of the env region of the HTLV-III virus. Such cells may be cloned and cultured by methods now well-known in the art so as to provide a continuous source of the desired monoclonal antibody.

Any conventional immuno assay method now known in the art may be employed using the antibodies of the invention. For example, a suitable radioimmunoassay method utilizing the above described reagents can be carried out by mixing a sample containing the HTLV-III virus with a known amount of the labelled tyrosine analog of formula I and the HTLV-III (578–608) env protein specific monoclonal or polyclonal antibody, measuring the degree of binding of the labelled analog and determining the amount of AIDS virus present in said sample by comparing said degree of binding to a standard curve obtained by mixing known amounts of AIDS virus with fixed amounts of said labelled analog and said antibody and determining the degree of binding for each known amount of virus or viral protein.

Another diagnostic embodiment of the invention provides a radioimmune assay for detecting the presence of AIDs antibodies in sera. In such assay sera samples are serially diluted in buffer and mixed with a radio iodinated analog of a peptide of formula I where W is Tyr. After incubation, anti-human IgG is added and the mixture incubated again. After centrifugation, the radioactivity bound to the precipitated antibody complex is measured. The presence of AIDs antibody is detected by count values in excess of those observed as background for normal patient sera.

In a further diagnostic aspect of the invention, an immunometric assay procedure may be run utilizing the antibodies of the present invention produced above. In a representative embodiment of such assay method duplicate samples are run. The procedure employs 100 $\mu l$ of a suspension of antibody immobilized on Agarose particles mixed with 100 $\mu l$ of serum and 100 $\mu l$ of soluble $^{125}$I-labelled antibody. This mixture is allowed to incubate for a time period ranging from $\frac{1}{4}$ hour to 24 hours. Following the incubation, the Agarose particles are washed by addition of buffer and then centrifuged. After removal of the washing liquid by aspiration, the resulting pellet of Agarose particles is then counted for bound $^{125}$I-labelled antibody. The counts obtained for each of the complexes can then be compared to controls.

In a further diagnostic embodiment antigen (chemically synthesized peptides corresponding to formula I) is coated onto polystyrene microtiter plates. Excess antigen is removed by washing and the plates are blocked to prevent nonspecific binding. To the coated and blocked antigen plates, patient samples, positive and negative controls are added and allowed to incubate at 37° C. for 30 minutes. The plates are washed to remove unbound antibodies and then goat anti-human immunoglobulins coupled to horseradish peroxidase (HRP) are added. The HRP conjugate is allowed to react for 30 minutes at 37° C. and then the plates are washed to remove untreated HRP conjugate. HRP substrate, orthophenylene diamine dihydro chloride (OPD), is added to the plate and allowed to react for 15 minutes at room temperature. The enzyme reaction is terminated by addition of $H_2SO_4$ and the resulting yellow-brown color produced by the HRP is read on a spectrophotometer. The optical density read at 490 nm indicates the presence of HRP-conjugate bound to the human IgG which is in turn bound to the antigen on the plate.

In a further aspect of the present invention, the peptides of formula I particularly those having W or Z as cysteine can be incorporated into vaccines capable of inducing protective immunity against the AIDS virus. Known techniques may be employed for enhancing the antigenicity of such peptide vaccine preparations, for example, by coupling such peptide through the cysteine moiety to a toxoid such as diptheria toxoid or tetanus toxoid. It is also possible to couple such peptides to inorganic carrier materials which enhance immunogenicity by presenting such peptides to the host subject in the manner approximating the normal antigen on the viral surface. Such inorganic carrier materials include aluminum hydroxide. It is within the skill of the art to use such vaccine composition in combination with adjuvants or other enhancers of immune response, such as, immune interferon, interleukin-2, thymosin alpha 1 and the like. In addition, the vaccine composition may comprise other antigens to provide immunity against other diseases in addition to AIDS, such as, for example, hepatitis core or surface antigens. It is also within the skill of the art to produce a vaccine composition incorporating the peptides of the present invention into liposomes as a means of maintaining the peptides in a desirable orientation for inducing immunity in a host.

Routes of administration, antigen dose, number and frequency of injections are all matters of optimization within the scope of ordinary skill in the art, particularly in view of the fact that there is experience in the art in providing protective immunity by injection of other related antigens to provide immunity in other viral infections. It is anticipated that the principal value of providing immunity to AIDS infection will be for those individuals who have had no previous exposure to AIDS, e.g., individuals who are in the high risk population, such as, homosexuals, drug addicts, Hatians and Central Americans, and individuals who may be receiving blood transfusions. It is also anticipated that temporary immunity for infants may be provided by immunization of mothers during pregnancy.

In further experiments it was found that polyclonal antibodies elicited from the same peptides coupled to keyhole limpet hemocyanin elicited in rabbits will immunoblot with recombinant HTLV-III env protein.

The above results indicate that peptides of formula I, as described above, will be suitable for use in the diagnostic assays and vaccine compositions described.

The present invention is further illustrated by the following examples. In such examples the abbreviation Tos means tosylate, 2Cz means 2-chlorocarbobenzoxy, OBzl means O-benzyl and Dmb means dimethylbenzyl'. Boc means tertbutyloxycarbonyl, Dcb is 2,6-dichlorobenzyl, $B^{31}$ means henzyl, and for means formyl.

EXAMPLE 1

Preparation of Boc-Val-Benzhydrylamine resin 1

Benzhydrylamine-resin (BHA) (5.0 g, 0.5-0.7 meg/g) was coupled with Boc-Val-OH (3.04 g, 14 mmol) in $CH_2Cl_2$ (25 mL) with dicyclohexylcarbodiimide (DCC) (2.88 g) for 18 hrs. The resultant BOC-Val-BHA-resin was washed with $CH_2Cl_2$ (2×75 mL), DMF (1×75 mL), MeOH (2×75 mL), $CH_2Cl_2$ (2×75 mL) and dried. An aliquot was hydrolyzed (1 mL of 6M propionic-HCl at 130° for 2 hours). Amino acid analysis showed a substitution of 0.33 mmol of Val per gram of resin. The remaining amino groups were acetylated with AC-2O-pyridine, yield: 5.36 g.

EXAMPLE 2

Preparation of HTLV-III env (578–608)-$NH_2'^2$

BOC-Val-BHA-resin (5.0 gg, 1.65 mmol) from Example 1 was charged into a reaction vessel clamped to a Model S-500 shaker equipped with an RD-20 shaker head (Kraft Apparatus, Inc., Minneola, N.Y.). Solid phase peptide synthesis was carried by the DCC procedure for a total of 30 cycles with the following $N^\alpha$-BOC amino acids: BOC Ala, BOC Thr(Bzl), BOC Thr(Bzl), BOC Cys(Dmb), BOC Ile, BOC Leu, BOC Lys(2-Cz), BOC Gly, BOC Ser(Bzl), BOC Cys(Dmb), BOC Gly, BOC Trp(For), BOC Ile, BOC Gly, BOC Leu, BOC Leu, BOC Gln, BOC Gln, BOC Asp(OBzl), BOC Lys(2 Cz), BOC Leu, BOC Tyr(Dcb), BOC Arg(Tos), BOC Glo(OBzl), BOC Val, BOC Ala, BOC Leu, BOC Ile, BOC Arg(Tos) and BOC-Ala to give 8.66 g of protected peptide resin. The protected peptide resin (1 g) was treated with anhydrous liquid HF containing 10% dithioethane at 0° for 1 hour. The HF was evaporated at 0° (high vac, CaO trap) and the crude peptide and resin mixture successing triturated with EtOAc, extracted with TFA, evaporated and the residue triturated with ether and dried, yield: 545 mg. The crude product was dissolved in 10 mL of $H_2O$ (containing 0.025% TFA), filtered (0.45μ type HA Millipore filter) and loaded into a Synchropak RP-P column (2×50 cm).

The column was eluted (4 mL/min.) with a solvent system consisting of (A) $H_2O$ (Containing 0.025% TFA) and (B) $CH_3CN$ (Containing 0.025% TFA) in a linear gradient mode: 20% B–45% B in 150 minutes. Fractions were collected (1 min./fraction) and aliquots analyzed by the analytical hplc system. The product emerged in fractions 99–104 which were combined, evaporated and lyophilized to give pure HTLV-III env (578–608)$NH_2$ yield: 22 mg. The product was shown to be homogeneous by analytical hplc and gave the expected amino acid composition (6N HCl; 1% TGA; 150°; 1 hour): Thr, 2.05; Ser, 1.05; Tyr, 0.90; *Trp, 0.60. (110°; 24 hours): Asp, 1.04; Glu, 2.70; Gly, 3.00; Ala, 2.85; Val, 1.95; Tyr, 0.90; Lys, 1.95. (72°; 110 hours): Ile, 2.65; Leu, 5.37; Arg, 1.98. *Trp partially destroyed.

EXAMPLE 3

Conjugation of HTLV-III env. (578–608)-$NH_2$ with Thyroglobulin, 3

Thyroglobulin (TG), (Bovine, Sigma type 1, 5 mg) was dissolved in 0.250 μl of 0.01M $NaH_2PO_4$ (ph 7.3) and a solution of m-maleimidobenzoyl-N-succinimide ester (MBS), (0.7 mg in 100 μl DMF) was added at 25° and the reaction mixture stirred (magnetically) for 30 minutes. The reaction mixture was charged into a Sephadex G-25 column (1.5×25 cm) which was previously equilibrated with 0.05M $NaH_2PO_4$ (pH 6.0). Fractions (1 mL/min.) were collected and the first major peak (280 nm detection) was pooled [MB-TG complex]. The HTLV-III env (578–608)-$NH_2$ peptide (5 mg) in 1 mL of 0.05M $NaH_2PO_4$ (pH 6.0) was added to the solution containing the MB-TG complex. The pH was adjusted to 7–7.5 by addition of 1.0N NaOH (μl amounts) and stirring proceeded at 25° for 3 hours. The heterogeneous mixture was dialyzed (MW cut-off 3500) against Dulbecco's phosphate buffered saline, with repeated changes, at 4° over a 72 hour period. The dialyzed solution (10 mL) was used directly in the Elisa assay.

EXAMPLE 4

Coating Procedure

Synthetic peptide, HTLV-III env (578–608) was suspended in 0.05M carbonate-bicarbonate buffer, pH 9.6, at a concentration of 1 mg/ml. This stock solution was further diluted to achieve a final concentration of 25 μg/ml. One hundred microliters of this solution was added to each well of a Falcon Pro-bind polystyrene microtiter plate (Falcon 3915). The plates were indubated at 37° C. for 16–18 hours. The plates are then washed 5 times with deionized water using an automatic plate washer. To reduce non-specific binding to the plate, 200 microliters of a 0.1M Tris-acetate buffer, pH 8.6, containing 1.0% Bovine Serum Albumin and 0.01% Thimerosal was added to each well. The plates were incubated at 37° C. for a minimum of one hour and washed 5 times with dionized water. These plates are now ready for use.

EXAMPLE 5

Elisa Procedure

All reagents are allowed to come to room temperature prior to use. Specimens are run at a 1:100 dilution. One ml of specimen diluent, containing 50% Normal goat serum (heat inactivated for 30 minutes at 56° C. and then sterile filtered) in phosphate buffered saline with 0.05% Tween 20 and 0.01% Thimerosal, is added to a test tube for each sample to be run. Ten microliters of sera/plasma specimen to be tested is added and mixed by vortexing and allowed to equilibrate for 5 minutes. One hundred μl of diluted specimen, positive control and negative control in duplicate are added to the plate. The positive and negative controls are prediluted positive (having antibodies to HTLV-3) and negative (no antibodies to HTLV-3) specimens. The specimens are allowed to incubate for 30 minutes at 37° C. The plates are then washed 2 cycles on an automatic washer (Skatron) using deionized water. One microliters of HRP-conjugate, Tris-acetate buffer containing 20% Fetal Calf Serum, 0.05% Tween 2.0, 0.01% Thimerosal and goat anti-human immunoglobulins coupled to Horse Radish Peroxidase (Boehringer-Mannheim), is added to each well using a multichannel pipettor. The plates are incubated at 37° C. for 30 minutes and washed as before. During the HRP conjugate incubation an enzyme-substrate solution is prepared using one OPD tablet in 5 ml buffer substrate solution (Roche). This reagent is light sensitive and must be protected from light. One hundred microliters of the enzyme substrate solution is added to each well and the plates are incubated at room temperature, in the dark, for 15 minutes. One hundred fifty microliters of stopping solution (1N $H_2SO_4$) is added to each well to terminate the reaction. The plates are scanned at 490 nm to determine the optical density of each well.

Results

Negative controls gave an optical density between 0.05–0.100 OD units. The Positive control gave OD's between 0.900–1,000 OD units. Samples giving ODs above 0.200 were considered positive in this Elisa.

Forty-five positive HTLV-3 sera (These samples were positive in a Commercial Elisa and confirmed by Western Blotting) and forty-five negative sera (commercial Elisa negative) were run in the peptide Elisa. The Elisa detected 45/45 positives (ODs ranged from 0.352 to >1.5 OD units) and 0/45 negatives (ODs ranged from 0..000 to 0.163 OD units) giving a sensitivity and specificity of 100%.

What is claimed is:

1. A peptide of the formula
   W-X-Ala-Arg-Ile-Leu-Ala-Val-Glu-Arg-Tyr-Leu-Lys-Asp-Gln-Gln-Leu-Leu-Gly-Ile-Trp-Gly-Cys-Ser-Gly-Lys-Leu-Ile-Cys-Thr-Thr-Ala-Val-Y-Z
   where W is H-, Cys- or Tyr, X is a bond, Y is a bond, and Z is —OH, —$NH_2$ or —Cys-$NH_2$.

2. The peptide of claim 1, wherein W is H- and Z is —$NH_2$.

3. An immunogenic composition for the generation of antibodies to peptides of Formula I comprising an immunogenically effective amount of a peptide of claim 1, where W is Cys or Z is Cys-$NH_2$, covalently bonded to an immunogenically compatible carrier material.

4. The composition of claim 3, wherein said immunogenic carrier material is thyroglobulin.

* * * * *